United States Patent

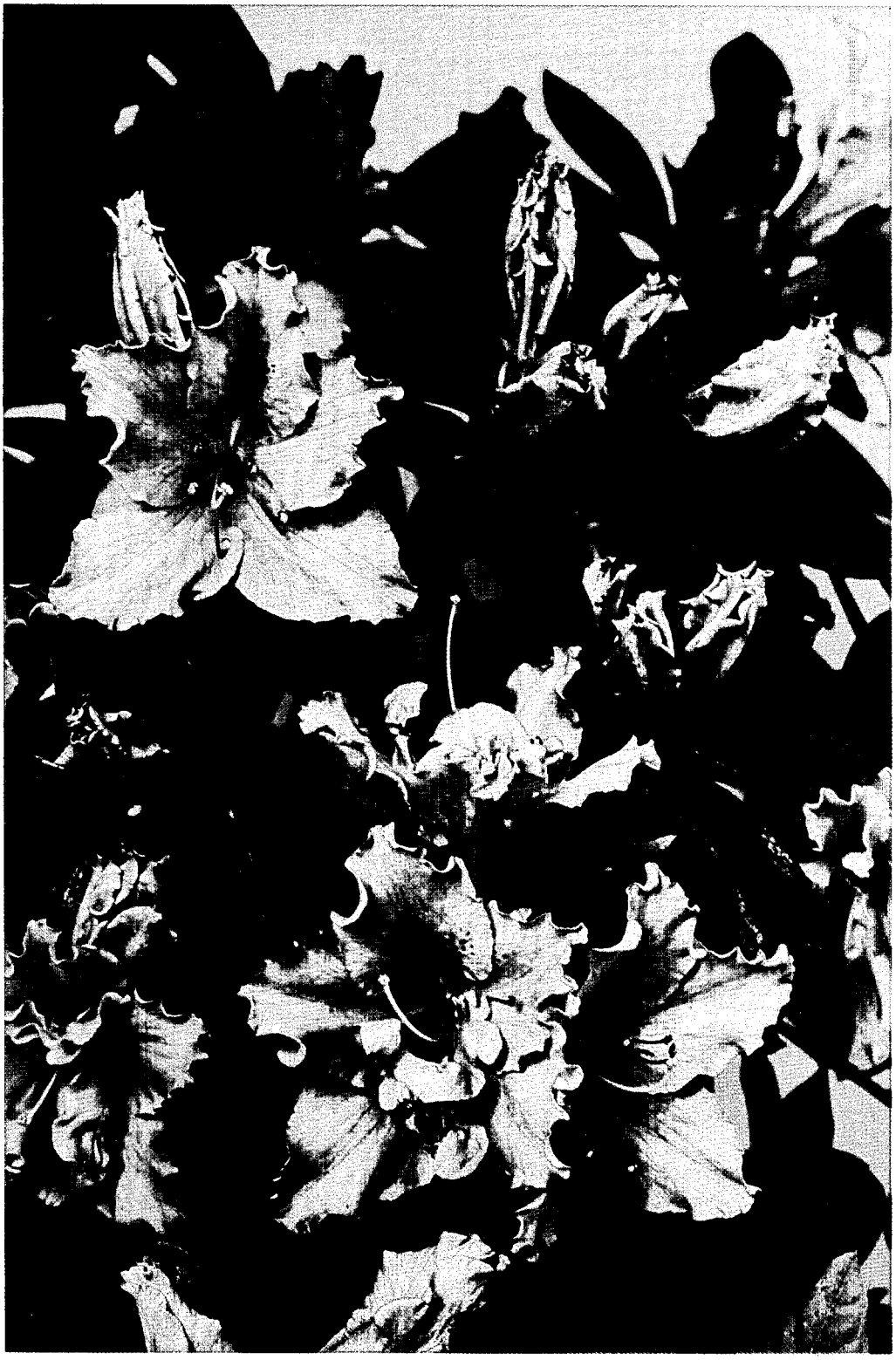

Plant Pat. 3,886

Patented May 18, 1976

3,886

AZALEA PLANT

James W. Hines, Jr., Corona Del Mar, Calif., assignor to Hines Wholesale Nurseries, Santa Ana, Calif.

Filed Nov. 25, 1974, Ser. No. 526,618

Int. Cl. A01h *5/00*

U.S. Cl. Plt.—57 1 Claim

The present invention relates to a new and distinct variety of azalea plant. This plant was originated by me in March 1957, by crossing the azalea variety of the Southern Indica strain, Azalea "Twilight" (unpatented) with the azalea variety of the Belgian Indica strain, Azalea "Twilight"/Azalea "Wm. Van Orange" (unpatented). The seeds which were produced by this hydridization were first sown in September 1957, and the plant first bloomed in March 1958.

As a result of this breeding, I have produced a new and improved azalea variety which is endowed with the following unique combination of characteristics which are outstanding therein, and which distinguish the same from its parents, as well as from all other varieties of which I am aware.

The plant is characterized as to novelty by its ability to grow and flower in full sun or light shade in the southern California area without tip burning of the leaves or blasting of the flowers; by its abundant and rich green foliage and compact and dense habit of growth; by the unique coloring of its flowers; and by its profuse flowering.

The new variety has been asexually reproduced by me on my cultivated property on the Irvine Ranch, near Santa Ana, Calif. Several hundred cuttings of this new and distinct variety have been made since March 1963, and it holds its distinguishing characteristics through succeeding propagations.

The drawings which accompany this petition show a typical view of the flowers and foliage of my new azalea variety. These are portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: On the Irvine Ranch, approximately 5 miles south of Santa Ana, Calif.

Parentage: Seedling resulting from planned propagation.

*Seed parent.*—Azalea "Twilight," an unpatented variety of the Southern Indica strain.

*Pollen parent.*—Azalea "Twilight"/Azalea "Wm. Van Orange," an unpatented variety of the Belgian Indica strain.

THE PLANT

Growth: The plant is of very vigorous growth habit, with dense branching starting just above ground level. Flowering is prolific, with first blooms in late November, and heaviest bloom from late February into March. The plant is suitable for forcing. This plant has a stronger growth habit than the Belgian Indica variety, with plants in the nursery growing to a height of three feet.

Branches: New growth is in the Greyed-Orange Group, Plates 165B to 165C, gradually changing color toward the tip to the Yellow-Green Group, Plates 144B to 144C. Older branches are in the Greyed-Orange Group, Plates 177B to 177C. All branches are hirsute.

Foliage: The leaves are of good substance, semi-glossy to glossy and abundant.

Shape: Elliptic with an acute tip. Leaf Margins are entire and slightly hairy.

Color:

*New leaves.*—Upper surface is in the Yellow-Green Group, Plates 144A to 144B. Underside is in the Yellow-Green Group, Plates 144B to 144C.

*Mature leaves.*—Upper surface is in the Yellow-Green Group, Plates 147A to 147B. Underside is in the Yellow-Green Group also, Plates 147B to 147C.

Size: New leaves range from ⅝ to ¾ inch in width, and 2 to 2⅛ inches in length. Mature leaves range from ⅞ to 1 inch in width, and 2⅜ to 2½ inches in length.

Veins: Prominent and lighter in color than leaf, running from the petiole to the tip, and having pinnate veins extending therefrom.

THE FLOWER

The plant first flowers in late November, with heaviest bloom in late February, extending to mid-March, with occasional blooming thereafter. The flowers are borne 3 to 7 to a stem, regularly clustered, with flowers appearing at both the tips of the branches, and also to mid-branch, creating a very floriferous effect.

Form: Flowers are single, with a tendency for some to be semi-double.

Petals: Corolla lobes are frilled. There are five corolla lobes when single and five corolla lobes and two to five metamorphosed stamens when semi-double. At maturity, the blossoms range from 3¼ to 3½ inches in width and from 1⅞ to 2 inches in depth.

Color: The colors of the flowers are entirely in the Red-Purple Group, with fluorescent-like sheen. The color tones range gradually from Plates 68B to 68C at the base of the corolla tube, to a range between plates 58B and 58D and Plates 74A to 74B toward the petal lobes. The standard and wing petals have blotches ranging from Plates 60A to 60B.

Buds: Long, tapered, and in the Red-Purple Group, ranging from between Plates 58A and 58B to between Plates 74B and 74C.

Reproductive organs: 6 stamens with color in the Red-Purple Group, Plates 74B to 74C. They range from 1½ to 2 inches in length. Pollen—Greyed-Yellow Group, Plates 162B to 162C.

I claim:

1. A new and distinct variety of azalea plant which is a hybrid of the Belgian Indica strain and the Southern Indica strain, and characterized in particular to novelty by its ability to grow and flower in full sun or light shade in the southern California area without tip burning of the leaves or blasting of the flowers; by its abundant and rich green foliage and compact and dense habit of growth; by the unique fluorescent-like color of its flowers; and by its profuse flowering; and by its greater salts tolerance, making it less subject to root diseases common to other varieties grown in the same general area of the Irvine Ranch in southern California.

References Cited

The Azalea Handbook, Lee et al., 1952, Amer. Hort. Society, pp. 13–14, plate 3 cited.

ROBERT E. BAGWILL, Primary Examiner